(12) United States Patent
Romanytsia

(10) Patent No.: US 12,247,964 B2
(45) Date of Patent: Mar. 11, 2025

(54) CHEMICAL CAPTURE SYSTEM WITH INTEGRATED CALIBRATION AND METHOD OF USING SUCH A SYSTEM

(71) Applicant: ELLONA, Toulouse (FR)

(72) Inventor: Ivan Romanytsia, Toulouse (FR)

(73) Assignee: ELLONA, Toulouse (FR)

( * ) Notice: Subject to any disclaimer, the term of this patent is extended or adjusted under 35 U.S.C. 154(b) by 295 days.

(21) Appl. No.: 18/000,867

(22) PCT Filed: Jun. 29, 2021

(86) PCT No.: PCT/EP2021/067920
§ 371 (c)(1),
(2) Date: Dec. 6, 2022

(87) PCT Pub. No.: WO2022/002979
PCT Pub. Date: Jan. 6, 2022

(65) Prior Publication Data
US 2023/0213491 A1 Jul. 6, 2023

(30) Foreign Application Priority Data

Jul. 1, 2020 (FR) ..................................... 2006965

(51) Int. Cl.
*G01N 33/00* (2006.01)
(52) U.S. Cl.
CPC ..... *G01N 33/0006* (2013.01); *G01N 33/0032* (2013.01); *G01N 33/0039* (2013.01)
(58) Field of Classification Search
CPC .......... G01N 33/0006; G01N 33/0032; G01N 33/0039
See application file for complete search history.

(56) References Cited

U.S. PATENT DOCUMENTS

| 2014/0284222 | A1* | 9/2014 | Wanek, Jr. | ............. | G01N 21/61 250/336.1 |
| 2015/0369784 | A1 | 12/2015 | Friedrich | | |
| 2019/0265183 | A1 | 8/2019 | Brown et al. | | |
| 2021/0231626 | A1* | 7/2021 | Di Benedetto | .... | G01N 33/0006 |

FOREIGN PATENT DOCUMENTS

DE 102017002764 A1 9/2018

OTHER PUBLICATIONS

International Search Report and Written Opinion on corresponding PCT application (PCT/EP2021/067920) from International Searching Authority (EPO) dated Sep. 22, 2021.

* cited by examiner

*Primary Examiner* — Paul M. West
(74) *Attorney, Agent, or Firm* — Alumen IP Law PC

(57) ABSTRACT

A method for using a chemical capture system with integrated calibration having a chamber which comprises an opening and a closing member, as well as a chemical sensor to be calibrated and a photoionization sensor which are positioned in the chamber, in which method: —during a measurement step, the sensor to be calibrated and the photoionization sensor measure the gas mixture present in the chamber, defining an open interior space, so as to identify the gas mixture and—during a calibration step, the photoionization sensor generates ozone by photoionizing the dioxygen in the chamber, defining a closed interior space free of gas mixture, and the sensor to be calibrated measures the generated ozone, the difference between said measurement and a reference measurement making it possible to calibrate said sensor.

10 Claims, 6 Drawing Sheets

CHEMICAL CAPTURE SYSTEM WITH INTEGRATED CALIBRATION AND METHOD OF USING SUCH A SYSTEM

TECHNICAL FIELD

The present invention relates to the field of chemical capture systems with integrated calibration and the use of such systems.

BACKGROUND

In a known manner, with reference to [FIG. 1], a chemical sensor 100 is configured to measure a physical signal C, such as the concentration, of one or more chemical compound(s) 60, 61 of a gaseous mixture 6, depending on its sensitivity. For this purpose, a chemical sensor 100 comprises a measuring element 101 configured to emit an electrical signal U which is a function of the quantity of the gaseous mixture 6 and an element for calculating the concentration C from the electrical signal U emitted and a conversion function f, specific to the chemical sensor 100 and stored in a database 103, according to the following relationship: C=f(U). In a known manner, a chemical sensor 100 must be calibrated before it is used for the first time. For this purpose, the chemical sensor 100 is placed in several standard media corresponding to known gaseous mixtures of which the concentrations are known. The difference between the concentration C measured by the chemical sensor 100 and the actual concentration of chemical compounds of each standard medium is corrected by modifying the conversion function f of the chemical sensor 100 to reduce this difference.

In fact, the response of a chemical sensor 100 drifts during use, notably when the chemical sensor 100 is in the form of a semiconductor sensor or an electrochemical sensor. More precisely, for an identical gaseous mixture 6, the measuring element 101 of the chemical sensor 100 emits a different electrical signal U as it is used. Indeed, in the case of a semiconductor sensor, also called "MOX sensor" or "MOS sensor", the measuring element 101 comprises a metal oxide layer heated by a heating element, on which the chemical compounds 60, 61 of the gaseous mixture 6 become fixed, this phenomenon being known as "adsorption". The measuring element 101 further comprises measuring electrodes configured to emit an electrical signal U corresponding to an electrical conductivity of the metal oxide layer. However, as the semiconductor sensor is used, absorption of the chemical compounds 60, 61 clogs the pores of the metal oxide layer, which changes the emitted electrical signal U.

Such a sensor 100 must therefore be calibrated regularly to ensure that the measured concentration C remains reliable and accurate. In practice, calibration is carried out by adjusting the conversion function f so that it takes account of the drift of the electrical signal U in the calculation of the concentration C. This requires quantifying the drift of the electrical signal U, which is achieved by placing the sensor 100 in several standard media and measuring the difference between the concentration C measured by the chemical sensor 100 and the actual chemical concentration of each standard medium. Such calibration during the lifetime of the sensor 100 requires uninstalling then re-installing the sensor 100 in contact with the gaseous mixture 6, which is costly in time and in resources. Further, if carrying out the calibration is forgotten or delayed or if the sensor 100 is unexpectedly out of adjustment, a false concentration C may be measured without knowing it.

Incidentally, an ozone capture system with integrated calibration comprising a chamber and an electrochemical ozone sensor and an ozone generator placed in the chamber is known. During a measurement phase, the chamber is opened so as to guide the gaseous mixture whose ozone concentration it is wished to measure to the sensor. During a calibration phase, the chamber is closed and the ozone remaining in the chamber is decomposed by contact with the chamber walls. The ozone generator is then configured to emit a known concentration of ozone into the closed chamber that is measured by the electrochemical sensor. The difference between the ozone concentration measured by the electrochemical sensor and emitted by the ozone generator is used to calibrate the sensor. Such a system advantageously allows calibration without moving the sensor. However, it has the drawback of being operable only for the particular case of a sensor sensitive only to ozone. In fact, for a sensor that is also sensitive to volatile organic compounds, abbreviated as "VOCs", VOCs may remain trapped in the closed chamber during calibration. Such VOCs falsify the calibration because they do not decompose like ozone, are present in unknown concentrations, and the sensor measures them in the same way as ozone without distinction.

It is also known by the patent application US2019265183A1 a gas capture system with integrated calibration comprising an enclosure in which a sensor, a heating plate to reset it, a light source and a heating element are mounted. The heating element allows ozone to be decomposed in the enclosure to calibrate the sensor in baseline and the light source allows ozone to be generated in a known concentration to complete the calibration. The elements dedicated to the calibration have the drawback of increasing the bulk of the system, particularly in measurement periods when they are inactive, and to increase the risk of maintenance. In addition, in the event of the sensor being unexpectedly out of adjustment, a false concentration may be measured without knowing it.

Furthermore, it is known by the patent application US2015369784A1 to calibrate a MOX sensor by comparing its measurement to that of a photoionization sensor, mounted on a different circuit and switched on only during a calibration period. Such a solution has the same drawbacks as before.

The invention thus aims to eliminate at least some of the stated drawbacks related to the calibration of a chemical sensor.

SUMMARY

The invention relates to a method of using a chemical capture system with integrated calibration for measuring a gaseous mixture, said system comprising:
- a chamber delimiting an inner volume and comprising at least one opening for fluidic communication of the gaseous mixture and the inner volume and at least one member for closing said opening moveably mounted between a closed position delimiting a closed inner volume and an open position delimiting an open inner volume,
- at least one chemical sensor, called the sensor to be calibrated, positioned in the inner volume of the chamber and comprising a measuring element configured to emit an electrical signal which is a function of the quantity of at least one predetermined chemical compound in the inner volume, said sensor to be calibrated comprising an element for calculating a first physical signal (C1) of said chemical compound from said electrical signal (U1) and a conversion function (f) specific to said sensor to be calibrated according to the following relationship: C1=f(U1), at least one photoionization sensor positioned in the inner volume, deemed not to be subject to drift and configured, on the one hand, to emit ultraviolet rays so as to photoionize at least one predetermined chemical compound in the inner volume, and, on the other hand, to determine a second physical signal which is a function of the quantity of said photoionized chemical compound, and at least one control device, method in which, in at least one measurement step:

the control device controls the movement of the closing member in the open position so that the chamber delimits an open inner volume into which the gaseous mixture enters, the sensor to be calibrated and the phototoionization sensor respectively measure at least one first physical measurement signal and at least one second physical measurement signal of the gaseous mixture, and the control device identifies the gaseous mixture from the physical measurement signals.

The invention is remarkable in that, during at least one calibration step:

the control device controls the movement of the closing member in the closed position so that the chamber delimits a closed inner volume, when the closed inner volume is free of gaseous mixture and ozone, the photoionization sensor generates ozone in the closed inner volume by emitting ultraviolet rays according to a given power, configured to photoionize the dioxygen present, the sensor to be calibrated measures a physical calibration signal of the ozone generated, the control device calculates the difference between the physical calibration signal and a physical reference signal, and if the difference is greater than a reference difference, the control device determines an optimized conversion function from said difference for the sensor to be calibrated, in order to calibrate it.

Thanks to the invention, it is possible to use a chemical capture system to fulfill two functions, namely to measure a gaseous mixture and to calibrate a chemical sensor. Such an internal calibration of the sensor within the chemical capture system avoids human handling to move the sensor into known standard media to carry out the calibration, which is more convenient and faster, such handling having above all to be repeated regularly. In addition, the calibration is performed using in an innovative manner the measurement means, and notably the photoionization sensor, which reduces the bulk and the cost of the chemical capture system. More precisely, the photoionization sensor making it possible to complete the measurement of the sensor to be calibrated during a measurement step is usefully used in a second function as an ozone generator during a calibration step, by photoionizing the dioxygen naturally present in the air. In other words, in addition to its sensor function, the photoionization sensor makes it possible to create in the closed inner volume a known calibration medium with a certain quantity of ozone to calibrate the sensor to be calibrated, that is to say a predetermined calibration concentration. Such a photoionization sensor is reliable because it is not subject to drift. The implementation of the calibration step after a measurement step, and vice versa, is further simple and fast, governed by the control device that moves the closing member from the open position to the closed position, and vice versa.

According to one aspect, the system comprising at least one device for removing the gaseous mixture in the inner volume, during the calibration step, the device removes any potentially residual gaseous mixture in the inner volume before the generation of ozone. The device for removing the gaseous mixture advantageously allows the calibration step to be implemented at any time, in the presence or not of a gaseous mixture, by removing it in a preliminary manner.

According to a first aspect of the invention, the chamber comprising at least one inlet opening and at least one outlet opening, the capture system comprises at least one ventilation member mounted in the chamber, preferably at the outlet opening, and at least one member for filtering the gaseous mixture moveably mounted at the inlet opening between a deployed position and a retracted position and forming, with the ventilation member, the device for removing the gaseous mixture, the removal of the gaseous mixture during the calibration step being implemented in the open inner volume by the control device by jointly controlling the movement of the filtering member to the deployed position and the activation of the ventilation member, so as to avoid the admission of gaseous mixture into the open inner volume and to evacuate any potentially residual gaseous mixture out of the open inner volume.

Such a removal of the gaseous mixture in the open inner volume of the chamber is simple and convenient to implement, using reduced means at low cost, namely the filtering member, in conjunction with the means of circulation and renewal of the gaseous mixture, namely the ventilation member. Such a removal is also effective and fast, particularly for a small chamber, the gaseous mixture being blocked at the inlet opening and discharged at the outlet opening.

According to a second aspect of the invention, the photoionization sensor forming the device for removing the gaseous mixture, the removal of the gaseous mixture during the calibration step is implemented in the closed inner volume by the photoionization sensor by emitting ultraviolet rays configured, on the one hand, to generate ozone by photoionization of the dioxygen present in order to react by ozonolysis with any potentially residual gaseous mixture in the inner volume, and, on the other hand, to photoionize said gaseous mixture.

Such a removal of the gaseous mixture in the closed inner volume of the chamber advantageously uses the photoionization sensor according to a third function of device for removing the gaseous mixture, further to its first function as a measurement sensor and its second function as an ozone generator. Such a removal of the gaseous mixture is also effective and fast, by the combined action of ozonolysis and photoionization. In other words, the photoionization sensor allows the gaseous mixture to be removed in two ways via the ultraviolet rays it emits: predominantly indirectly by generating ozone that reacts with the gaseous mixture by ozonolysis, and in a minority directly by photoionization of the gaseous mixture. The gaseous mixture thus removed by photoionization and ozonolysis is advantageously not detected by the sensor to be calibrated.

According to one aspect of the invention, during the measurement step, the first physical measurement signal and the second physical measurement signal are measured simultaneously. As the concentration of the gaseous mixture may change over time, this ensures that the gaseous mixture measured by the sensor to be calibrated and the photoionization sensor is identical, and therefore that their measurements can be crossed to accurately and reliably identify the gaseous mixture at a given time(s).

According to another aspect of the invention, during at least one initialization step:
- the control device controls the movement of the closing member in the closed position so that the chamber delimits a closed inner volume,
- when the closed inner volume is free of gaseous mixture and ozone, the photoionization sensor generates ozone in the closed inner volume by emitting, according to said given power, ultraviolet rays configured to photoionize the dioxygen present; and
- the sensor to be calibrated measures said physical reference signal of the ozone generated.

Advantageously, such an initialization period makes it possible to determine a physical reference signal forming a reliable and accurate source of comparison for the physical calibration signal. Indeed, the physical reference signal is measured when the sensor to be calibrated is considered valid. In addition, the physical reference signal is of the same nature as the physical calibration signal, notably measured in the same medium—the closed inner volume of the chamber being free of the gaseous mixture to be measured and comprising ozone of known and identical concentration, and by the same measuring device—the sensor to be calibrated.

Preferably, during the removal step, the removal device removes any potentially residual gaseous mixture in the inner volume, in an analogous manner to the calibration step. This allows the initialization step to be set at any time, with or without the gaseous mixture present.

Preferably, the method of use comprises a single initialization step, preliminary to any measurement and calibration step. The physical calibration signal obtained is therefore used as a basis for comparison for all the calibration steps.

Preferably, the method of use comprises an alternation of measurement and calibration steps. The interest of such a chemical capture system with integrated calibration is to measure the gaseous mixture and, when necessary, to interrupt the measurement to carry out a calibration. Preferably, the calibration steps are carried out regularly to keep the drift of the sensor to be calibrated low.

The invention also relates to a chemical capture system with integrated calibration for measuring a gaseous mixture, said system comprising:
- a chamber delimiting an inner volume and comprising at least one opening for fluidic communication of the gaseous mixture and the inner volume and at least one member for closing said opening moveably mounted between a closed position delimiting a closed inner volume and an open position delimiting an open inner volume,
- at least one chemical sensor, called the sensor to be calibrated, positioned in the inner volume of the chamber and comprising a measuring element configured to emit an electrical signal which is a function of the quantity of at least one predetermined chemical compound in the inner volume, said sensor to be calibrated comprising an element for calculating a first physical signal ($C1$) of said chemical compound from said electrical signal ($U1$) and a conversion function ($f$) specific to said sensor to be calibrated according to the following relationship: $C1=f(U1)$, said sensor to be calibrated being configured in particular to determine, respectively, during a measurement step and during a calibration step of the method of use as previously described, a first physical signal for measuring the gaseous mixture in the open inner volume and a physical signal for calibrating ozone in the closed inner volume,
- at least one photoionization sensor positioned in the inner volume and configured, on the one hand, to emit ultraviolet rays so as to photoionize at least one predetermined chemical compound in the inner volume, and, on the other hand, to determine a second physical signal which is dependent on the quantity of said photoionized chemical compound, said photoionization sensor being in particular configured, during the measurement step, to determine a second physical signal for measuring the gaseous mixture in the open inner volume and, during the calibration step, to emit ultraviolet rays according to a given power to photoionize dioxygen into ozone in the closed inner volume, and
- at least one control device configured to control the movement of the closing member to the open position during the measurement step, so that the chamber delimits an open inner volume, and to the closed position during the calibration step, so that the chamber delimits a closed inner volume, said control device being configured:
- during the measurement step, to identify the gaseous mixture from the first and second physical measurement signal, and
- during the calibration step, to calculate the difference between the physical calibration signal and a physical reference signal and, if the difference is greater than a reference difference to determine an optimized conversion function for the sensor to be calibrated, so that it can be calibrated.

Such a chemical capture system with integrated calibration advantageously forms a unitary set of two functions, namely for measurement and calibration. Such a capture system further has a limited bulk and cost, using the same means for measurement and for calibration. In particular, the photoionization sensor is used on the one hand as a measuring sensor and on the other hand as a generator of ozone from the dioxygen naturally present in the air.

Preferably, the system further comprises at least one device for removing the gaseous mixture in the inner volume of the chamber, so that calibration can be implemented at any time in the presence or absence of residual gaseous mixture in the inner volume.

According to one aspect of the invention, the chamber comprises at least one inlet opening, at least one outlet opening and at least one member for closing the inlet opening and the outlet opening, in order to facilitate the circulation of the gaseous mixture in the open inner volume. Such a chamber comprising an inlet opening and an outlet opening allows a reliable and accurate measurement of the gaseous mixture during the measurement step of the method of use. Indeed, the inlet opening and the outlet opening generate a circulation of the gaseous mixture and thus prevent any local stagnation of the gaseous mixture. The sensor to be calibrated and the photoionization sensor thus measure a global and non-local concentration of the gaseous mixture in the air.

According to another aspect of the invention, the chemical capture system comprises at least one ventilation member mounted in the chamber, preferably at the outlet opening, to promote the renewal of the gaseous mixture in the open inner volume. Such a ventilation member thus improves the reliability and accuracy of the measurement of the sensor to be calibrated and the photoionization sensor.

According to one preferred aspect, the chemical capture system comprises at least one member for filtering the gaseous mixture moveably mounted at the inlet opening between a deployed position and a retracted position. Such a filtering device advantageously forms, with the ventilation member, the device for removing the gaseous mixture. Such a removal device is simple, of limited cost and allows the removal of the gaseous mixture in an open inner volume.

According to another preferred aspect, the photoionization sensor forms the device for removing the gaseous mixture. Such a removal device does not have additional bulk and allows the gaseous mixture to be removed in a closed inner volume.

Preferably, the sensor to be calibrated is in the form of a non-selective sensor, sensitive at least to the gaseous mixture to be measured and to ozone. Such a sensor is subject to drift and must be calibrated regularly, which the chemical capture system allows for in a simple and practical manner According to one aspect of the invention, the sensor to be calibrated is in the form of a semiconductor sensor or an electrochemical sensor. The chemical capture system is advantageously suited for a large number of sensors to be calibrated of different nature and sensitivity.

BRIEF DESCRIPTION OF THE DRAWINGS

The invention will be better understood upon reading the following description, given solely as an example, and by referring to the accompanying figures, given as non-limiting examples, wherein identical references are given to similar objects and wherein.

It should be noted that the figures disclose the invention in detail in order to implement the invention, said figures can of course be used to better define the invention if necessary.

DETAILED DESCRIPTION

Figure 1:
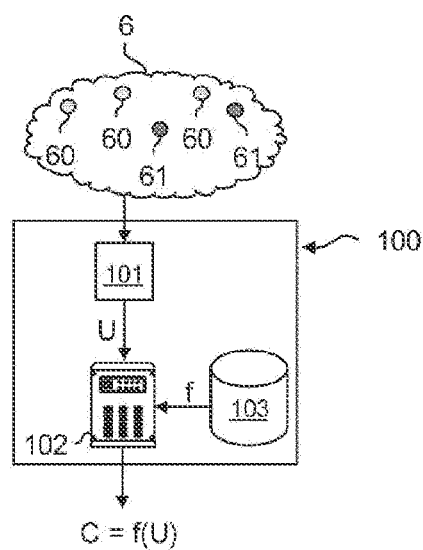
FIG. 1 is a schematic representation of a chemical sensor.
Figure 2:
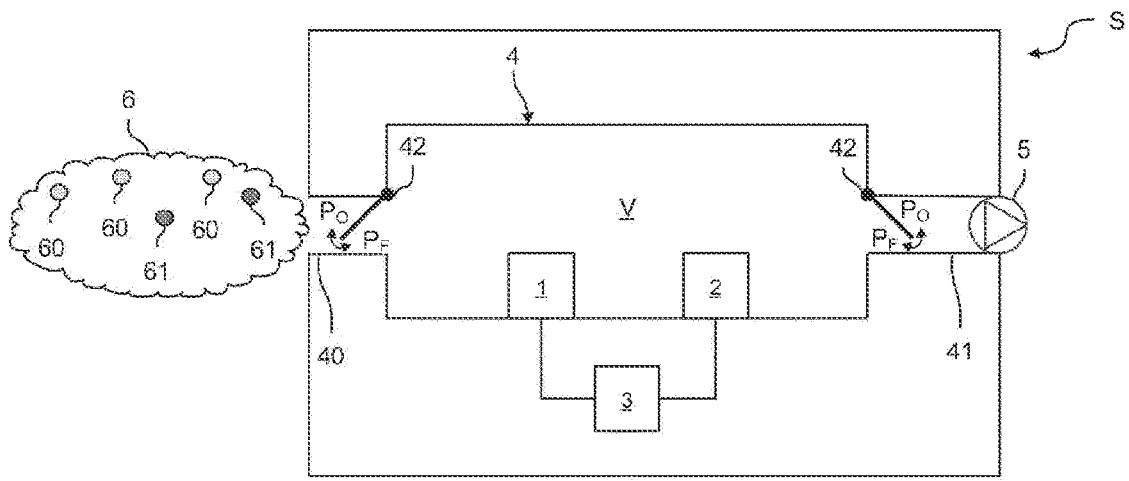
FIG. 2 is a schematic representation of the chemical capture system with integrated calibration according to one embodiment of the invention.

With reference to [FIG. 2], the invention relates to a chemical capture system with integrated calibration S allowing, according to a first use, the identification of a gaseous mixture 6 via the measurement of a chemical sensor 1, and, according to a second use, the calibration of said chemical sensor 1. As an example, the system S is mounted in an office and configured to identify a gaseous mixture 6 in the form of pollutants, such as volatile organic compounds, emitted by human occupancy, in the ambient air of the office.

Figure 5:
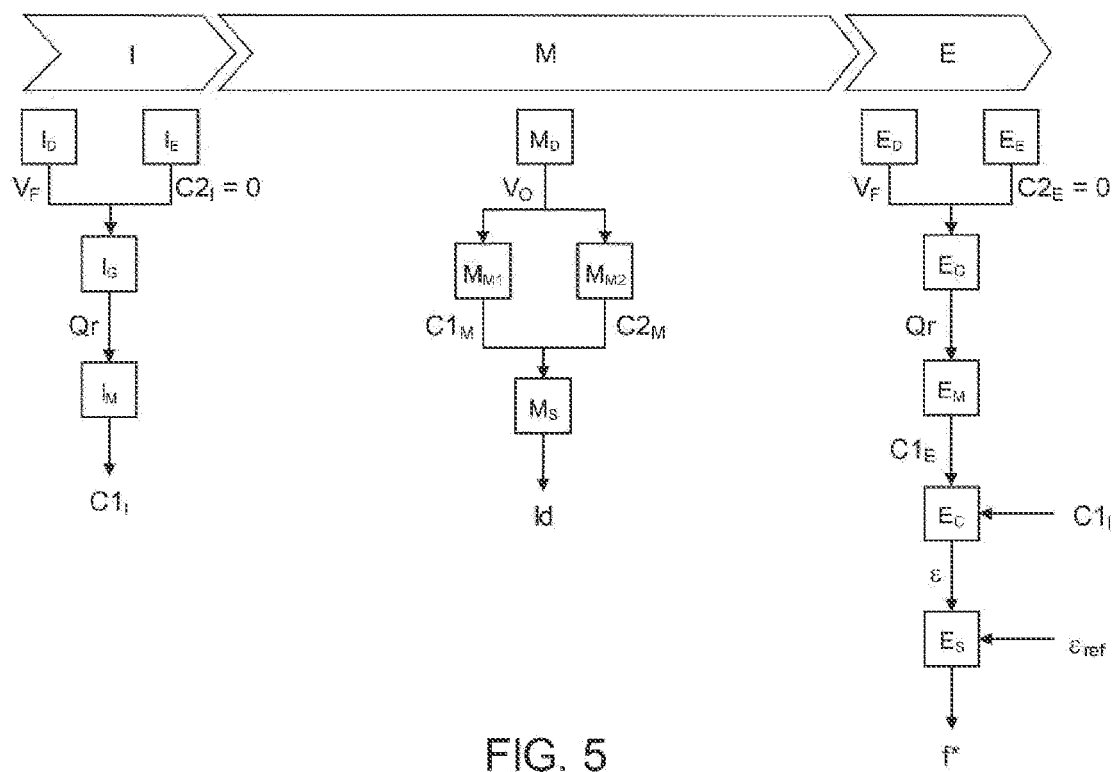
FIG. 5 is a schematic representation of the method of using the chemical capture system of [FIG. 2] according to one embodiment of the invention.

Hereafter, the structural and functional characteristics of the system S are described, followed by its method of use, through an initialization step I, a measurement step M and a calibration step E (see [FIG. 5]).

According to the invention and as known illustrated in [FIG. 2], the chemical capture system S comprises:

- a chamber 4 delimiting an inner volume V and comprising one (or more) opening(s) 40, 41 and a member for closing 42 each opening 40, 41,
- one (or more) chemical sensor(s) 1, hereinafter referred to as sensor(s) to be calibrated 1, and one (or more) photoionization sensor(s) 2 positioned in the inner volume V of the chamber 4,
- a control device 3 of the system S for implementing the initialization, measurement and calibration steps, and
- in some embodiments of the invention, a device for removing the gaseous mixture 6 in the inner volume V of the chamber 4.

The chamber 4, the sensors to be calibrated 1 and the photoionization sensors 2, the device for removing the gaseous mixture 6 and the control device 3 are successively described hereafter.

In the example of [FIG. 2], the chamber 4 comprises two openings, namely an inlet opening 40 and an outlet opening 41, allowing the admission of the gaseous mixture 6 into the inner volume V as well as its expulsion. It should be noted that each opening 40, 41 allows the circulation of the gaseous mixture 6 to be identified, such as pollutants, but also of the ambient air in which it is located, such as the ambient air of an office in which the chamber is mounted. It should be noted that the inlet opening 40 and the outlet opening 41 are preferably positioned opposite each other to promote the circulation of the gaseous mixture 6 throughout the inner volume V of the chamber 4. The openings 40, 41 thus contribute to ensuring that the gaseous mixture 6 in contact with the sensor to be calibrated 1 and the photoionization sensor 2 is representative of the gaseous mixture 6 throughout the entire inner volume V, thus enabling a relevant measurement and reliable identification. It goes without saying that the chamber 4 could comprise a different number of openings, notably a single opening to allow the entry and exit of the gaseous mixture 6 in order to limit the bulk.

Still with reference to [FIG. 2], to improve the circulation and renewal of the gaseous mixture 6 in the inner volume V of the chamber 4, in this example the system S comprises a ventilation member 5 mounted in the chamber 4, preferably at the outlet opening 41. As an example, the ventilation member 5 is in the form of a fan or suction pump. It goes without saying that the ventilation member 5 may not be present or may be mounted differently in certain embodiments of the invention, notably to limit the bulk.

According to the invention and still with reference to [FIG. 2], each closing member 42 is moveably mounted between a closed position $P_F$ (suited for the initialization and calibration steps) and an open position $P_O$ (suited for the measurement step). In the closed position $P_F$, the chamber 4 delimits a closed inner volume $V_F$ (see [FIG. 7A]), preferably in a leaktight manner to avoid any admission of fluid external to the chamber 4 and any fluidic backflow out of the chamber 4. In the open position $P_O$, the chamber 4 delimits an open inner volume $V_O$ (see [FIG. 6A]), that is to say allowing fluidic admission into the chamber 4, notably of gaseous mixture 6, and fluidic backflow out of the chamber 4. In the example of [FIG. 2], each closing member 42 is in the form of a flap, pivotally mounted so that in the closed position $P_F$ the flap blocks the opening 40, 41 and that in the open position $P_O$, the inner volume V is in fluidic communication with the gaseous mixture 6. It goes without saying that the closing member 42 could be moved according to other kinematics, notably a translation. The closing member 42 could also be in another form, notably that of a valve.

Still with reference to [FIG. 2], the chamber 4 preferably has reduced dimensions, slightly larger than those of the sensor to be calibrated 1 and the photoionization sensor 2. Preferably, the chamber 4 has a volume of less than 10 cm³. This facilitates the action of the device for removing the gaseous mixture 6 in the inner volume V as will be described below. Such a chamber 4, and therefore the system S, further has a small bulk, which makes it easy and convenient to install in any type of environment.

Figure 3:
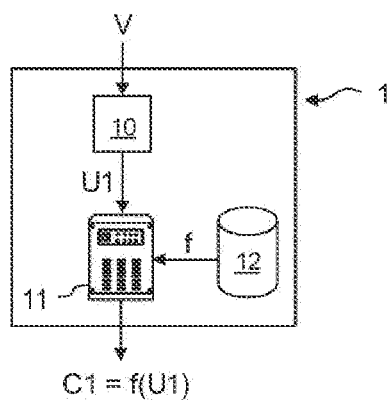
FIG. 3 is a schematic representation of the sensor to be calibrated of the chemical capture system of [FIG. 2]

According to the invention and with reference to [FIG. 3], in a known manner the sensor to be calibrated 1 comprises:
    a measuring element 10 configured to emit an electrical signal U1 which is a function of the quantity of one (or more) predetermined chemical compound(s) in the inner volume V; and
    an element for calculating 11 a first physical signal C1 of said chemical compound from said electrical signal U1 and a conversion function f specific to said sensor to be calibrated 1, stored in this example in a database 12, according to the following relationship: C1=f(U1).

In practice, the sensor to be calibrated 1 is chosen sensitive at least to the gaseous mixture 6 to be measured, and more precisely to at least one predetermined chemical compound 60, 61 of the gaseous mixture 6 (see [FIG. 2]), as well as to ozone, as will be explained below. The sensor to be calibrated 1 is thus configured to emit a physical signal C1, such as a concentration by way of example, of the gaseous mixture 6 and the ozone present in the inner volume V of the chamber 4. Furthermore, the sensor to be calibrated 1 is, as its name suggests, subject to drift, that is to say for an identical gaseous mixture 6, the measuring element 10 of the sensor to be calibrated 1 emits a different electrical signal U1 as it is used. In other words, the conversion function f is no longer representative of the relationship between the electrical signal U1 and the corresponding physical signal C1.

Preferably, the sensor to be calibrated 1 is in the form of a non-selective sensor, that is to say sensitive to a plurality of chemical compounds, so that the system S is suited to measuring a wide range of gaseous mixtures 6. Such a system S further enables precise identification of the gaseous mixture 6, thanks to the photoionization sensor 2, which is notably configured to measure a second physical signal of the gaseous mixture 6, in addition to the first physical signal C1, as will be described below.

For example, the sensor to be calibrated 1 is in the form of a semiconductor sensor, also known as the MOX sensor or MOS sensor, for which the measuring element 10 comprises a metal oxide layer heated by a heating element, on which the chemical chemicals 60, 61 of the gaseous mixture 6 become fixed, known as adsorption. The measuring element 10 further comprises measuring electrodes configured to measure an electrical signal U1 corresponding to an electrical conductivity of the metal oxide layer. For such a sensor, the drift is notably generated by the gradual clogging of the pores of the metal oxide layer, which changes its electrical conductivity. Alternatively, the sensor to be calibrated 1 is in the form of an electrochemical sensor. Such sensors are known per se to those skilled in the art and will not be described further.

According to one preferred aspect, the sensor to be calibrated 1 is chosen sensitive to volatile organic compounds, abbreviated as "VOCs", in the air. VOCs designates, by way of example, pollutants emitted by means of transport, printers, radiators, smoking, burning candles or emissions emitted during ripening of fruits and vegetables, and notably formaldehyde, ethanol, acetone, acetaldehyde, benzene, toluene and xylene. In other words, the gaseous mixture 6 to be identified is in the form of VOCs. The sensor to be calibrated 1 is thus in the form of a sensor non-selective to a single chemical compound.

Figure 4:
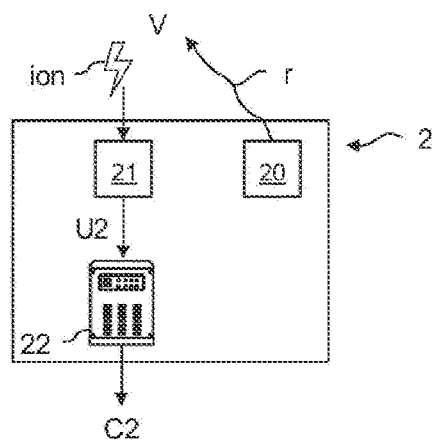
FIG. 4 is a schematic representation of the photoionization sensor of the chemical capture system of [FIG. 2]

According to the invention and with reference to [FIG. 4], in a known manner, the photoionization sensor 2 comprises:
    an emitter 20 of ultraviolet rays r in the inner volume V, such as a light source by way of example, configured to photoionize one (or more) predetermined chemical compound(s) in the inner volume V,
    a measuring element 21, such as measuring electrodes for example, configured to emit an electrical signal U2 which is a function of the quantity of the photoionized chemical compound; and
    an element for calculating 22 a second physical signal C2 of said photoionized chemical compound from said electrical signal U2.

In practice, the photoionization sensor 2 is configured to emit a second physical signal C2 of the gaseous mixture 6, such as a concentration of VOC for example, to complement the first physical signal C1 measured by the sensor to be calibrated 1. The emitting power of the emitter 20 of ultraviolet rays r is thus chosen sufficiently large to photoionize the gaseous mixture 6 and sufficiently low for the photoionization sensor 2 to be selective. In addition to its measurement sensor function, the photoionization sensor 2 is also configured according to a second function (suited for the calibration step) to generate ozone in the inner volume V. More precisely, the emitter 20 is configured to provide an emitting power of ultraviolet rays r so as to photoionize the dioxygen naturally present into ozone. The emitting power of ultraviolet rays r suitable for the calibration is preferably greater than that suitable for the measurement.

It should be noted that in the example shown in [FIG. 2], the system S comprises a single sensor to be calibrated 1 and a single photoionization sensor 2 to limit the bulk and the cost. However, it goes without saying that the system S could comprise a plurality of sensors to be calibrated 1, in particular sensitive to different gaseous mixtures 6 to increase the measuring range of the system S. The system S could also comprise several photoionization sensors 2, notably, so that each sensor to be calibrated 1 is associated with a photoionization sensor 2.

As previously described, the system S comprises in some embodiments a device for removing the gaseous mixture 6 being, in the example shown in [FIG. 2], in the form of the photoionization sensor 2. Indeed, the photoionization sensor 2, and more precisely the emitter 20 of ultraviolet rays r, also enables according to a third function the gaseous mixture 6 to be removed in the inner volume V and to do so in two combined ways:
- a first "direct" way, by photoionizing the gaseous mixture 6, namely by transforming it into ions by definition, and
- a second "indirect" way, by generating ozone O by photoionization of the dioxygen D naturally present in the air, which reacts by ozonolysis with the gaseous mixture 6.

In practice, ozonolysis makes it possible to remove most of the gaseous mixture 6 present in the inner volume V, namely about 90% of the gaseous mixture 6 present, and photoionization to remove the remaining part, which allows effective and fast removal. Thus, the photoionization sensor 2 is advantageously configured to fulfill three functions, namely that of the measurement of the gaseous mixture 6, that of ozone generator and that of removal of the gaseous mixture 6, which advantageously reduces the bulk and the cost.

Figure 7A:
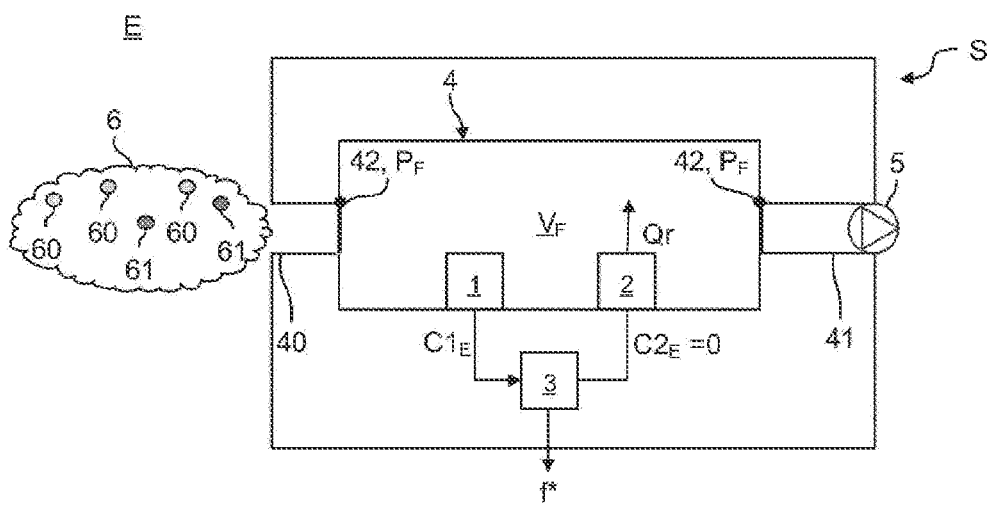
FIG. 7A is a schematic representation of the chemical capture system of [FIG. 2] during a calibration step.
Figure 7B:
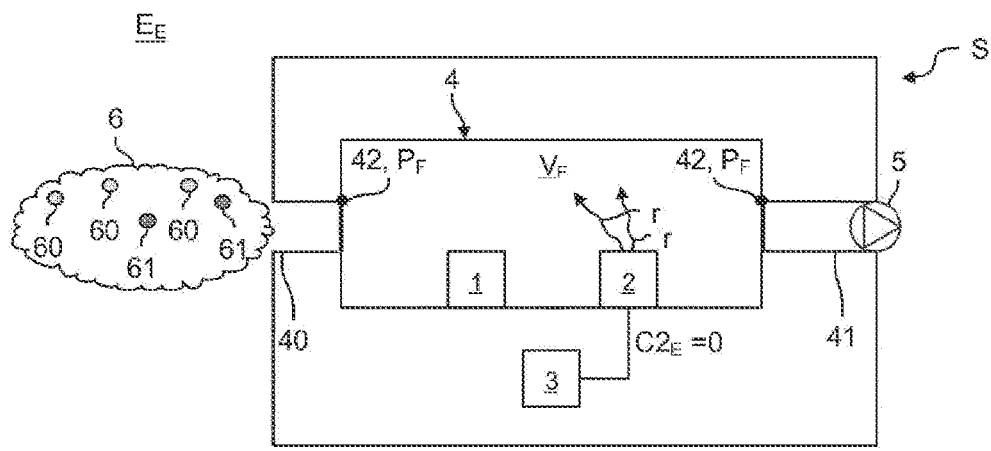
FIG. 7B is a schematic representation of the removal of the gaseous mixture during the calibration step of [FIG. 7A] according to a first embodiment of the invention.
Figure 7C:
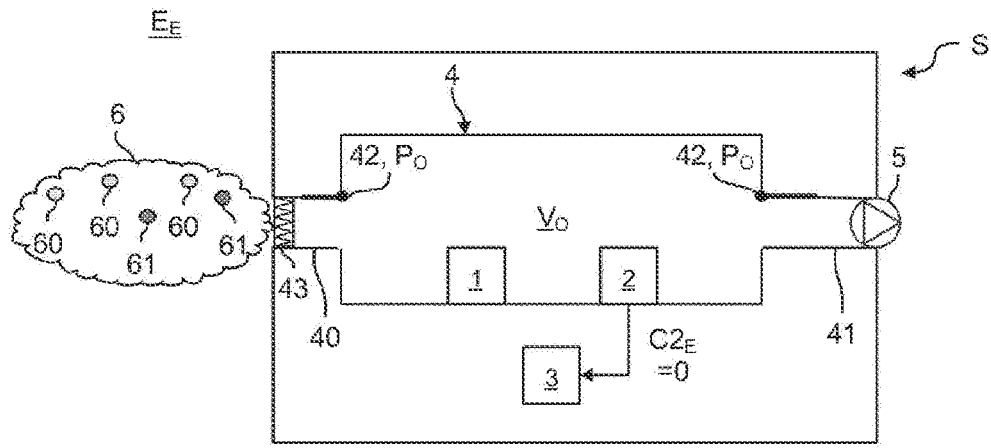
FIG. 7C is a schematic representation of the removal of the gaseous mixture during the calibration step of [FIG. 7A] according to a second embodiment of the invention.

Alternatively, the device for removing the gaseous mixture 6 is in the form of the ventilation member 5 in conjunction with a filtering member 43 (see [FIG. 7C]). The ventilation member 5 is preferably mounted in this alternative at the outlet opening 41 and is configured to evacuate the gaseous mixture 6 to the outside of the chamber 4. The filtering member 43 is for its part moveably mounted at the inlet opening 40 between a deployed position, in which it is configured to filter the gaseous mixture 6 admitted into the inner volume V, and a retracted position, in which the gaseous mixture 6 freely enters the inner volume V of the chamber 4, that is to say without filtering. The nature of the filtering member 43 depends on the gaseous mixture 6 to be measured. As an example, the filtering member 43 is in the form of a chemical filter configured to react with the gaseous mixture 6 or a physical filter configured to adsorb the gaseous mixture 6. Such filtering devices 43 are known per se to those skilled in the art and will not be described further. Such a device for removing the gaseous mixture is advantageously not complex and is efficient, preventing at the inlet opening 40 the admission of the gaseous mixture 6 and favoring at the outlet opening 41 the evacuation of potentially residual gaseous mixture 6 from the inner volume V.

Alternatively, the system S is free of a device for removing the gaseous mixture 6, the calibration being implemented at a convenient time when the gaseous mixture 6 is not present.

Still with reference to [FIG. 2], the control device 3 is preferably in the form of a computer calculator which preferably comprises a memory. The control device 3 is configured to control the movement of the closing members 42, and according to certain embodiments, the movement of the filtering member 43. The control device 3 is also configured to identify the gaseous mixture 6 from the measurements of the sensors to calibrate 1 and photoionization sensors 2 during a measurement step and, during a calibration step, to determine an optimized conversion function f for the sensor to be calibrated 1, as explained below.

To summarize, the system S of the invention comprises a sensor to be calibrated 1 and a photoionization sensor 2 positioned in a chamber 4, delimiting an open or closed volume, free or not of a gaseous mixture 6 to be measured and controlled by a control device 3. To save cost, time and bulk, the photoionization sensor 2 is multifunctional: it allows the identification of the gaseous mixture 6 in cooperation with the sensor to be calibrated 1, and when the sensor 1 needs to be calibrated, it forms an ozone generator to create a standard medium in the chamber 4.

The method of using the system S is described hereafter, which enables according to a first use the identification of a gaseous mixture 6, which corresponds in [FIG. 5] to a measurement step M, and according to a second use the calibration of the sensor to be calibrated 1, which corresponds in the same [FIG. 5] to a calibration step E.

With reference to [FIG. 5], the measurement step M and the calibration step E are implemented consecutively and not simultaneously. In practice, when using the system S, the measurement step M is implemented until a calibration is required for the sensor to be calibrated 1. For example, a calibration is required after noting a gaseous mixture 6 has been identified incorrectly or inaccurately, or after a predetermined period of use from which the sensor to be calibrated 1 is likely to drift. The measurement step M is then stopped to start the calibration step E. Once the calibration step E is completed, that is to say once the sensor 1 is calibrated, a new measurement step M is implemented. In practice, the method of using the system S thus comprises an alternation of measurement steps M and calibration steps E.

In the example of [FIG. 5], the method of using the system S comprises in addition a preliminary initialization step I which, as will be described below, increases the accuracy and reliability of the calibration step(s) E.

A measurement step M, a calibration step E and an initialization step I are described hereafter successively.

Figure 6A:
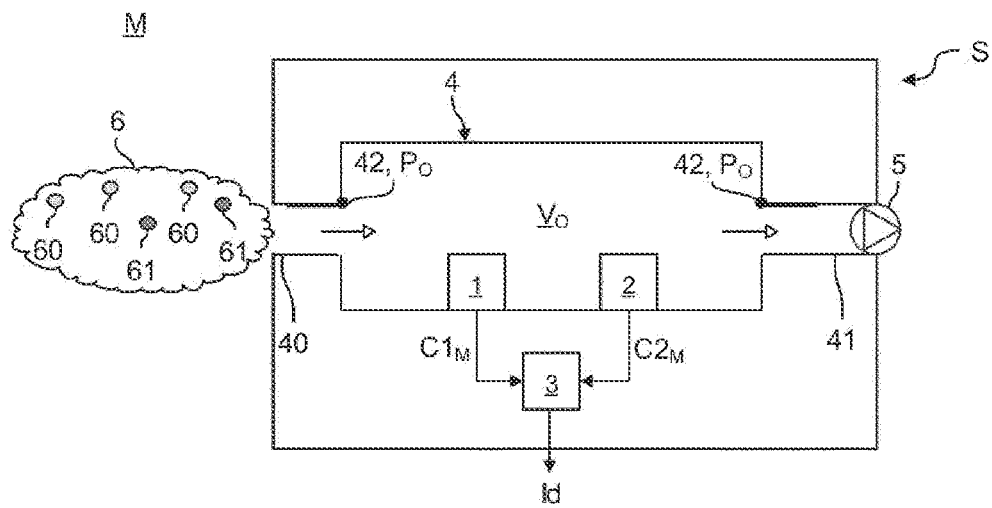
FIG. 6A is a schematic representation of the capture system of [FIG. 2] during a measurement step.

According to the invention and with reference to FIGS. 5 and 6A, during a measurement step M:
- the control device 3 controls the movement $M_D$ of the closing members 42 in the open position $P_O$ so that the chamber 4 delimits an open inner volume $V_O$ into which the gaseous mixture 6 enters,
- the sensor to be calibrated 1 and the photoionization sensor 2 measure $M_{M1}$, $M_{M2}$ respectively a first physical measurement signal $C1_M$ and a second physical measurement signal $C2_M$ of the gaseous mixture 6, and
- the control device 3 identifies $M_S$ the gaseous mixture 6 from the physical measurement signals $C1_M$, $C2_M$.

When the inner volume is open $V_O$, the gaseous mixture 6 flows in contact with the sensor to be calibrated 1 and the photoionization sensor 2, which allows an accurate and reliable measurement of the concentration of the gaseous mixture 6 present throughout the chamber 4 and not locally. In the example of [FIG. 6A], the control device 3 also controls the activation of the ventilation device 5 to promote the circulation and renewal of the gaseous mixture 6 in the chamber 4. It should be noted that each closing member 42 in the open position $P_O$ allows the gaseous mixture 6 to be identified to circulate in the chamber 4, as well as the ambient air in which the gaseous mixture 6 is located. As an example, the chamber 4 is positioned in an office where human occupancy creates pollutants in the ambient air and is configured to admit the pollutant-laden ambient air into the open inner volume $V_O$, the pollutants forming the gaseous mixture 6 to be identified.

Figure 6B:
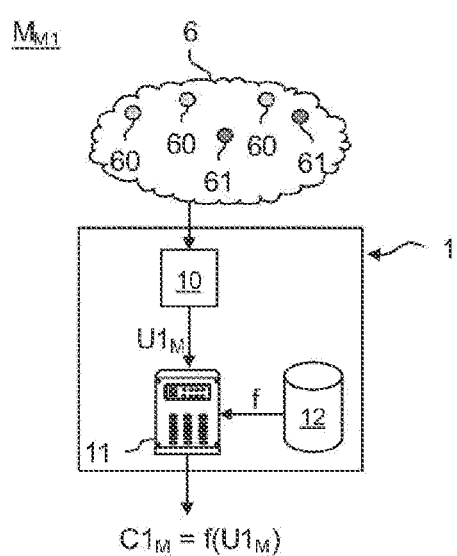
FIG. 6B is a schematic representation of the sensor to be calibrated from [FIG. 3] during the measurement step of [FIG. 6A]
Figure 6C:
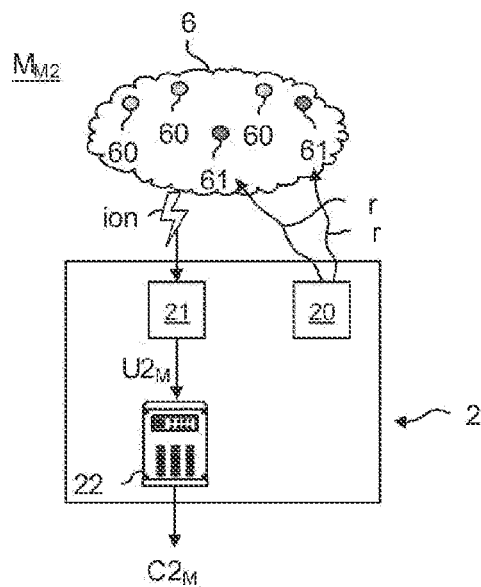
FIG. 6C is a schematic representation of the photoionization sensor of [FIG. 4] during the measurement step of [FIG. 6A]

Preferably, the two physical measurement signals $C1_M$, $C2_M$ are measured simultaneously so as to correspond to the same gaseous mixture 6. The physical measurement signals $C1_M$, $C2_M$ furthermore preferably correspond to averaged measurements to increase their reliability and accuracy, but it goes without saying that they may also be instantaneous measurements. With reference to FIGS. 6B and 6C, the physical measurement signals $C1_M$, $C2_M$ are obtained from electrical signals $U1_M$, $U2_M$ respectively. Such individual measurement steps are known to those skilled in the art.

With reference to [FIG. 5], the identification $M_S$ of the gaseous mixture 6 is implemented by comparing the physical measurement signals $C1_M$, $C2_M$ with a reference database. The identification is advantageously reliable and precise, because the second physical measurement signal $C2_M$ makes it possible to check the consistency and/or to complete the first physical measurement signal $C1_M$. In other words, the photoionization sensor 2 is deemed not subject to drift and allows a check of the measurement of the sensor to be calibrated 1. An inconsistency between the two physical measurement signals $C1_M$, $C2_M$ may notably reveal a drift of the sensor to be calibrated 1 and thus require the implementation of a calibration step E.

According to the invention and with reference to FIGS. 5 and 7A, during a calibration step E;
the control device 3 controls the movement $E_D$ of the closing members 42 in the closed position $P_F$ so that the chamber 4 delimits a closed inner volume $V_F$,
when the closed inner volume $V_F$ is free of gaseous mixture 6 and ozone O, the photoionization sensor 2 generates $E_G$ ozone O in the closed inner volume $V_F$ by emitting at a given power Qr ultraviolet rays r configured to photoionize the dioxygen D present,
the sensor to calibrate 1 measures $E_M$ a physical calibration signal $C1_E$ of the ozone O generated,
the control device 3 calculates $E_C$ the difference ε between the physical calibration signal $C1_E$ and a physical reference signal C1, and
If the difference ε is greater than a reference difference εref, the control device 3 determines an optimized conversion function f* for the sensor to be calibrated 1 from this difference ε in order to calibrate it.

It is specified that the dioxygen D naturally present in the chamber 4 comes from the ambient air admitted in the same way as the gaseous mixture 6, in practice before moving the closing members 42 to the closed position $P_F$.

In the embodiments illustrated in FIGS. 7B and 7C where the system S further comprises a device for removing the gaseous mixture 6, the calibration step in addition comprises, prior to the generation $E_G$ of ozone O, a removal $E_E$ of potentially residual gaseous mixture 6 in the inner volume V.

In practice, the movement $E_D$ of the closing members 42 is implemented before or after the removal $E_E$ of the gaseous mixture 6 according to the embodiments of the invention. In the example in [FIG. 7B] where the photoionization sensor 2 forms the device for removing the gaseous mixture 6, the movement $E_D$ of the closing members 42 is implemented first, so that the chamber 4 delimits a leaktight closed inner volume $V_F$. The photoionization sensor 2 then emits ultraviolet rays r in the closed inner volume $V_F$ in order to photoionize any gaseous mixture 6 that may be present.

In the example of [FIG. 7C] where the filtering member 43 and the ventilation member 5 together form the device for removing the gaseous mixture 6, the removal $E_E$ of the gaseous mixture 6 is implemented in the open inner volume $V_O$. To do this, the control device 3 moves the filtering member 43 to the deployed position so as to prevent the intake of the gaseous mixture 6 at the inlet opening 40. The control device 3 also controls the activation of the ventilation member 5 in order to evacuate any potentially residual gaseous mixture 6 in the inner volume V to the outside of the chamber 4. Once the gaseous mixture 6 has been removed $E_E$ in the chamber 4, the control device 3 moves the closing members 42 to the closed position $P_E$.

Preferably and as illustrated in FIGS. 7A to 7C, the removal $E_E$ of the gaseous mixture 6 is controlled by the photoionization sensor 2 by measuring a physical control signal $C2_E$ of the gaseous mixture 6 in the inner volume. If the physical control signal $C2_E$ corresponds to a substantially zero concentration of gaseous mixture 6, the calibration step E is continued. Alternatively, the removal $E_E$ is repeated until the chamber 4 is free of the gaseous mixture 6. It should be noted that the removal $E_E$ does not enable a vacuum to be formed in the chamber 4 but only removes the gaseous mixture 6 to be identified, the ambient air being still present.

Alternatively, the calibration step E is free of removal $E_E$ of the gaseous mixture 6 and is implemented at a suitable time, when the gaseous mixture 6 to be identified is not present in the inner volume V. In the example of a chamber 4 mounted in an office whose occupancy generates pollutants in the ambient air, the calibration step E is thus preferably implemented when the occupancy is low or zero. In other words, the calibration step E is preferably implemented when the air admitted into the chamber 4 is low-charged or not charged with a gaseous mixture 6 to be identified. Such a convenient time is determined by way of example thanks to the measurement history of the sensor to be calibrated 1 and the photoionization sensor 2.

Figure 7D:
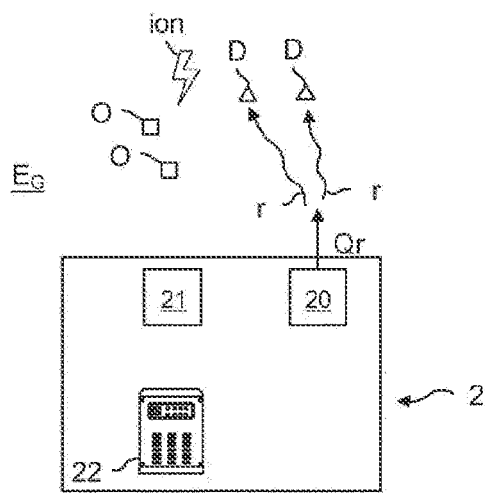
FIG. 7D is a schematic representation of the sensor to be calibrated of [FIG. 3] during the calibration step of [FIG. 7A]

With reference to [FIG. 7D], the generation $E_G$ of ozone O is implemented in a closed inner volume $V_F$ via an emission of ultraviolet rays r at a chosen given power Qr. The generation $E_G$ of ozone O thus enables the creation of a known standard medium in the chamber 4, that is to say of known ozone O concentration, via the emission power Qr, and of known gaseous mixture 6 concentration, namely substantially zero. In practice, for the closed inner volume $V_F$ to form a known standard medium, it must, prior to the implementation of the generation $E_G$ of ozone O, be free of gaseous mixture 6 and ozone O. For the gaseous mixture 6, this is done by preliminary removal $E_E$ or by choosing a suitable time for the calibration. The generation $E_G$ of ozone O is in addition preferably operated after a waiting time so that any potentially residual ozone O in the closed inner volume $V_F$ spontaneously decomposes in contact with the walls of chamber 4.

Figure 7E:
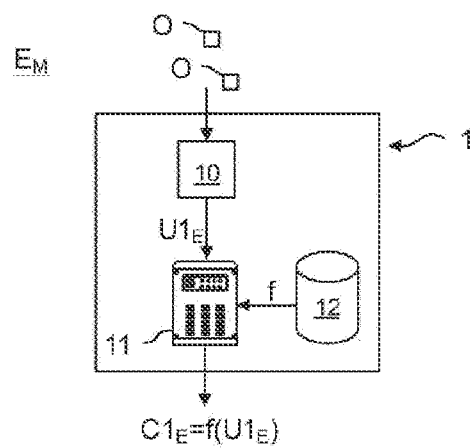
FIG. 7E is a schematic representation of the photoionization sensor of [FIG. 4] during the calibration step of [FIG. 7A]
Figure 7F:
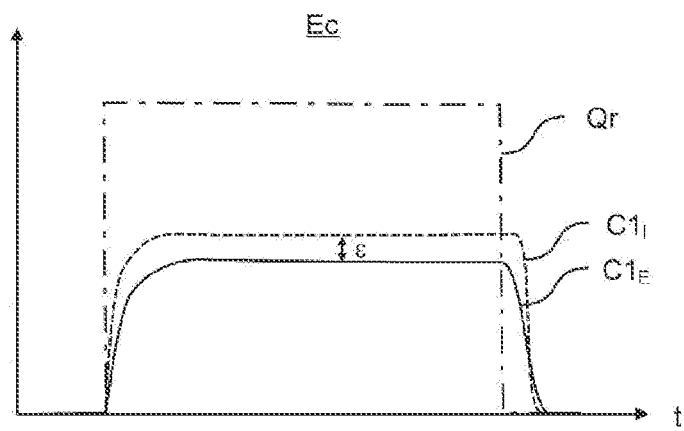
FIG. 7F is a schematic representation of the calculation of the difference between the concentration measured by the sensor to be calibrated during an initialization step and during the calibration step and FIG. 8 is a schematic representation of the chemical capture system with integrated calibration of [FIG. 2] during the initialization step.

With reference to [FIG. 7E], the physical calibration signal $C1_E$ measured by the sensor to be calibrated 1 in such a standard medium corresponds only to the ozone O present in the closed inner volume $V_F$, the concentration of which is known. With reference to [FIG. 7F], the control device 3 can thus calculate the drift potential of the sensor to be calibrated 1 by comparing the physical calibration signal $C1_E$ with a physical reference signal $C1_I$ of ozone O present in the same concentration. In the example of [FIG. 7F], the difference ε is obtained in the following manner: $\varepsilon = |C1_E - C1_I|/C1_I$. The reference difference εref is preferably chosen between 1% and 10%, preferentially of the order of 5%, in order to correct any significant drift of the sensor to be calibrated 1. In the event of drift, the optimized conversion function f* is calculated in the following manner: $f*(U1_E) = C1_I$.

Figure 8:
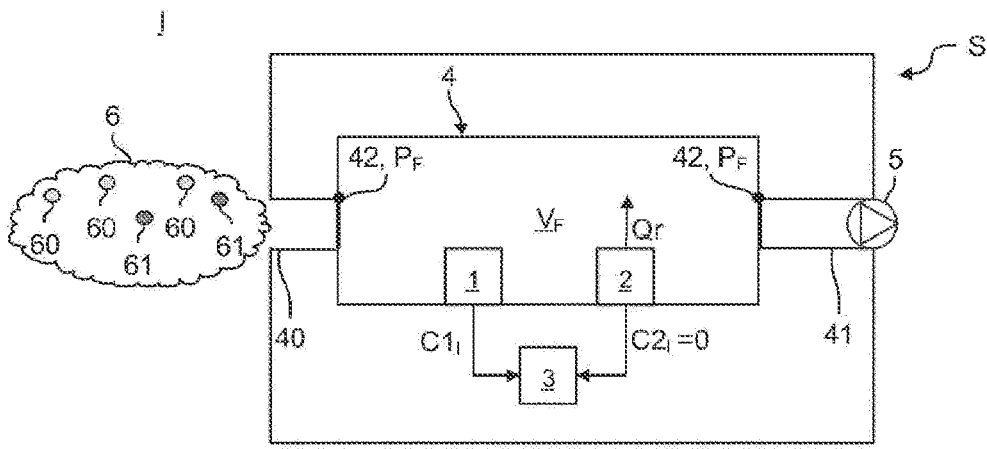

Preferably, the physical reference signal $C1_I$ is determined during the preliminary initialization step I of the method of using the system S. With reference to [FIG. 8], during such an initialization step I, the sensor to be calibrated 1 is considered valid and:

the control device 3 controls the movement $I_D$ of the closing member 42 in the closed position $P_F$ so that the chamber 4 delimits a closed inner volume $V_F$, when the closed inner volume $V_F$ is free of gaseous mixture 6 and ozone O, the photoionization sensor 2 generates $I_G$ ozone O in the closed inner volume $V_F$ by emitting, according to said given power Qr, ultraviolet rays r configured to photoionize the dioxygen D present and the sensor to be calibrated 1 measures $I_M$ said physical reference signal $C1_I$ of the ozone O generated.

In an analogous manner to the calibration step E, in the embodiments illustrated in FIGS. 7B and 7C where the system S further comprises a device for removing the gaseous mixture 6, the initialization step I in addition comprises, prior to the generation $I_G$ of ozone O, a removal $I_E$ of any potentially residual gaseous mixture 6 in the inner volume V.

Note the similarities between the initialization step I and the first four actions of the calibration step E. The initialization step I will thus not be described further, each of its actions being described by the action of the same name of the calibration step E to which reference is made. Such an initialization step I advantageously enables an accurate and reliable calibration of the sensor to be calibrated 1. Indeed, the physical reference signal $C1_I$ is measured in the same standard medium as the physical calibration signal $C1_E$, and with the same measuring means, namely the sensor to be calibrated 1. However, during the initialization step I, the sensor to be calibrated 1 is assumed to be calibrated in contrast to the calibration step E. The initialization step I is thus preferably implemented before the first measurement step M. It goes without saying that the physical reference signal $C1_I$ may be obtained in a different way, notably thanks to a database.

It should also be noted that in the case of chamber 4 comprising several sensors to be calibrated 1, a single sensor to be calibrated 1 is calibrated during a calibration step E and/or during an initialization step I. This makes it possible to avoid changing the standard medium and to ensure the reliability and accuracy of the calibration. The measurement step M may for its part be implemented with one or more sensors to be calibrated 1 simultaneously, to increase the accuracy and reliability of the identification of the gaseous mixture 6.

In summary, during a measurement step M using the system S, the sensor to be calibrated 1 and the photoionization sensor 2 each measure a physical measurement signal $C1_M$, $C2_M$ of the gaseous mixture 6 in the open inner volume $V_O$, which allows the control device 3 to discriminate the gaseous mixture 6. When a calibration E is required, the chamber 4 forms a known standard medium in which the sensor to be calibrated 1 measures a physical calibration signal $C1_E$ which, in comparison with a physical reference signal $C1_I$, allows correction of the potential drift of the sensor to be calibrated 1. The photoionization sensor 2 makes it possible, by ozonolysis and photoionization of any potentially residual gaseous mixture 6 in the chamber 4 and the dioxygen present, to remove the gaseous mixture 6 and to generate ozone O. Alternatively, the removal of the gaseous mixture 6 is implemented jointly by a filtering member 43 and a ventilation member 5.

According to one preferred aspect of the invention, the physical signals C1, C2 of the sensor to be calibrated 1 and of the photoionization sensor 2 are in the form of concentrations of the gaseous mixture 6 in the chamber 4. In other words, the first physical measurement signal $C1_M$ and the second physical measurement signal $C2_M$ preferably take the form of a first measurement concentration and a second measurement concentration of the gaseous mixture 6 in the chamber 4 respectively. The physical calibration signal $C1_E$ and the physical reference signal $C1_I$ of ozone O in the chamber 4 preferably take the form of an ozone calibration concentration and a reference ozone concentration respectively.

The invention claimed is:

1. A method of using a chemical capture system with integrated calibration for measuring a gaseous mixture, said system comprising:

a chamber delimiting an inner volume and comprising at least one opening for fluidic communication of the gaseous mixture and the inner volume and at least one member for closing said at least one opening moveably mounted between a closed position delimiting a closed inner volume and an open position delimiting an open inner volume, at least one chemical sensor, called sensor to be calibrated, positioned in the inner volume of the chamber and comprising a measuring element configured to emit an electrical signal (U1) which is a function of the quantity of at least one predetermined chemical compound in the inner volume, said at least one sensor to be calibrated comprising an element for calculating a first physical signal (C1) of said at least one chemical compound from said electrical signal (U1) and a conversion function (f) specific to said at least one sensor to be calibrated according to the following relationship: C1=f(U1), at least one photoionization sensor positioned in the inner volume, deemed not to be subject to drift, and configured, on the one hand, to emit ultraviolet rays so as to photoionize at least one predetermined chemical compound in the inner volume, and, on the other hand, to determine a second physical signal which is a function of the quantity of said at least one photoionized chemical compound, and at least one control device, method in which, during at least one measurement step:

the at least one control device controls the movement of the at least one closing member in the open position so that the chamber delimits an open inner volume into which the gaseous mixture enters, said at least one sensor to be calibrated and said at least one photoionization sensor measure respectively at least one first physical measurement signal and at least one second physical measurement signal of the gaseous mixture, and the at least one control device identifies the gaseous mixture from the at least one first and second physical measurement signals, method wherein during at least one calibration step:

the at least one control device controls the movement of the at least one closing member in the closed position so that the chamber delimits a closed inner volume, when the closed inner volume is free of gaseous mixture and ozone, said at least one photoionization sensor generates ozone in the closed inner volume by emitting according to a given power ultraviolet rays configured to photoionize the dioxygen present, said at least one sensor to be calibrated measures a physical calibration signal of the ozone generated, the at least one control device calculates the difference between the physical calibration signal and a physical reference signal, according to the given power of said at least one photoionization sensor, and if the difference is greater than a reference difference, the at least one control unit determines an optimized conversion function for said at least one sensor to be calibrated from this difference in order to calibrate it.

2. The method of use according to claim 1, wherein during the at least one calibration step, the system comprising at least one device for removing the gaseous mixture in the inner volume, the at least one removal device removes any potentially residual gaseous mixture in the inner volume before the generation of ozone.

3. The method of use according to claim 2, wherein, the chamber comprising at least one inlet opening and at least one outlet opening, the capture system comprises at least one ventilation member mounted in the chamber, and at least one member for filtering the mobile mounted gaseous mixture at the at least one inlet opening between an extended position and a retracted position forming with the at least one ventilation member the at least one device for removing the gaseous mixture, the removal of the gaseous mixture during the calibration step being implemented in the open inner volume by the at least one control device by jointly controlling the movement of the at least one filtering device in the deployed position and the activation of the at least one ventilation device, so as to avoid the admission of the gaseous mixture into the open inner volume and to evacuate any potentially residual gaseous mixture out of the open inner volume.

4. The method of use according to claim 2, wherein, said at least one photoionization sensor forming the at least one device for removing the gaseous mixture, the removal of the gaseous mixture during the calibration step is implemented in the closed inner volume by said at least one photoionization sensor by emitting ultraviolet rays configured, on the one hand, to generate ozone by photoionization of the dioxygen present in order to react by ozonolysis with any potentially residual gaseous mixture in the inner volume, and, on the other hand, to photoionize said gaseous mixture.

5. The method of use according to claim 1, wherein, during the at least one measurement step, the at least one first physical measurement signal and the at least one second physical measurement signal are measured simultaneously.

6. The method of use according to claim 1, wherein, during at least one initialization step:

the at least one control device controls the movement of the at least one closing member in the closed position so that the chamber delimits a closed inner volume, when the closed inner volume is free of gaseous mixture and ozone, said at least one photoionization sensor generates ozone in the closed inner volume by emitting, according to said given power, ultraviolet rays configured to photoionize the dioxygen present and said at least one sensor to be calibrated measures said physical reference signal of the ozone generated.

7. A chemical capture system with integrated calibration for measuring a gaseous mixture, said system comprising:

a chamber delimiting an inner volume and comprising at least one opening for fluidic communication of the gaseous mixture and the inner volume and at least one member for closing said at least one opening moveably mounted between a closed position delimiting a closed inner volume and an open position delimiting an open inner volume, at least one chemical sensor, called sensor to be calibrated, positioned in the inner volume of the chamber and comprising a measuring element configured to emit an electrical signal (U1) which is a function of the quantity of at least one predetermined chemical compound in the inner volume, said at least one sensor to be calibrated comprising an element for calculating a first physical signal (C1) of said chemical compound from said electrical signal (U1) and a conversion function (f) specific to said at least one sensor to be calibrated according to the following relationship: C1=f(U1), said at least one sensor to be calibrated being in particular configured to determine, respectively during a measurement step and during a calibration step of the method of use according to claim 1, a first physical measurement signal of the gaseous mixture in the open inner volume and a physical calibration signal of ozone in the closed inner volume, at least one photoionization sensor positioned in the inner volume and configured, on the one hand, to emit ultraviolet rays so as to photoionize at least one predetermined chemical compound in the inner volume and, on the other hand, to determine a second physical signal which is a function of the quantity of said photoionized chemical compound, said at least one photoionized sensor being in particular configured, during the measurement step, to determine a second physical measurement signal of the gaseous mixture in the open inner volume and, during the calibration step, to emit ultraviolet rays according to a given power to photoionize dioxygen into ozone in the inner volume, and at least one control device configured to control the movement of the at least one closing member in the open position during the measurement step, so that the chamber delimits an open inner volume, and in the closed position during the calibration step, so that the chamber delimits a closed inner volume, said at least one control device being configured:

during the measurement step, to identify the gaseous mixture from the first and second physical measurement signals and, during the calibration step, to calculate the difference between the physical calibration signal and a physical reference signal, as a function of the given power of said at least one photoionization sensor, and, if the difference is greater than a reference difference, to determine an optimized conversion function for said at least one sensor to be calibrated, in order to calibrate it.

8. The chemical capture system according to claim 7, wherein the chamber comprises at least one inlet opening, at least one outlet opening and at least one member for closing the at least one inlet opening and the at least one outlet opening, in order to facilitate the circulation of the gaseous mixture in the open inner volume.

9. The chemical capture system according to claim 7, comprising at least one ventilation member mounted in the chamber to promote the renewal of the gaseous mixture in the open inner volume.

10. The chemical capture system according to claim 7, wherein said at least one sensor to be calibrated is in the form of a semiconductor sensor or an electrochemical sensor.

* * * * *